(12) United States Patent
Yuan et al.

(10) Patent No.: US 7,988,935 B2
(45) Date of Patent: Aug. 2, 2011

(54) HANDHELD AND PORTABLE MICROFLUIDIC DEVICE TO AUTOMATICALLY PREPARE NUCLEIC ACIDS FOR ANALYSIS

(75) Inventors: Bob Yuan, Belmont, CA (US); Nima Aflaatooni, Berkeley, CA (US)

(73) Assignee: MicroFluidic Systems, Inc., Fremont, CA (US)

( * ) Notice: Subject to any disclaimer, the term of this patent is extended or adjusted under 35 U.S.C. 154(b) by 965 days.

(21) Appl. No.: 11/223,095

(22) Filed: Sep. 9, 2005

(65) Prior Publication Data
US 2006/0051252 A1 Mar. 9, 2006

Related U.S. Application Data

(60) Provisional application No. 60/608,999, filed on Sep. 9, 2004.

(51) Int. Cl.
*B01D 24/02* (2006.01)
*B01L 3/02* (2006.01)

(52) U.S. Cl. ........ 422/527; 422/501; 422/502; 422/513; 422/534; 422/535; 73/863.32; 73/864; 73/864.01

(58) Field of Classification Search .......... 422/100–101, 422/501–502, 513, 527, 534–535; 436/180; 73/863.32, 864, 864.01
See application file for complete search history.

(56) References Cited

U.S. PATENT DOCUMENTS

| | | | |
|---|---|---|---|
| 3,985,032 A * | 10/1976 | Avakian | 73/863.25 |
| 4,275,166 A | 6/1981 | McCollough et al. | 435/227 |
| 4,666,595 A | 5/1987 | Graham | 210/222 |
| 4,689,204 A * | 8/1987 | Buck et al. | 422/100 |
| 4,806,313 A | 2/1989 | Ebersole et al. | |
| 4,973,450 A * | 11/1990 | Schluter | 422/101 |
| 4,999,164 A * | 3/1991 | Puchinger et al. | 422/100 |
| 5,048,520 A | 9/1991 | Vago | 128/24 A |
| 5,234,809 A | 8/1993 | Boom et al. | 435/91 |
| 5,695,989 A * | 12/1997 | Kalamasz | 435/308.1 |
| 5,707,799 A | 1/1998 | Hansmann et al. | |
| 5,851,491 A * | 12/1998 | Moulton | 422/101 |
| 5,952,173 A | 9/1999 | Hansmann et al. | |

(Continued)

FOREIGN PATENT DOCUMENTS
WO WO 99/33559 A1 7/1999

(Continued)

OTHER PUBLICATIONS

"High Sensitivity PCR Assay in Plastic Micro Reactors", Jianing Yang et al., Physical Sciences Research Laboratories, Motorola Labs, Motorola, Inc., 7700 S. River Parkway, MD-ML34, Tempe, AZ 85284, USA, Revised Aug. 29, 2002, pp. 179-187.

(Continued)

*Primary Examiner* — Brian R Gordon
(74) *Attorney, Agent, or Firm* — Haverstock & Owens LLP (57) ABSTRACT

A handheld and portable extraction device is directed to a microfluidic-based system to be used in the field to extract and purify an analyte, preferably a nucleic acid, from a fluid-based sample. Preferably, the fluid-based sample is water-based. The fluid-based sample can also be a biological fluid sample. The handheld and portable extraction device includes a syringe-like device coupled to a purification chip. The purification chip is preferably included within a chip block which is removable from the remaining portion of the handheld and portable extraction device. The analyte collected within the purification chip can be later removed and collected for analysis.

28 Claims, 7 Drawing Sheets

U.S. PATENT DOCUMENTS

| | | | | |
|---|---|---|---|---|
| 6,087,183 | A | 7/2000 | Zaromb | 436/178 |
| 6,100,084 | A | 8/2000 | Miles et al. | 435/306.1 |
| 6,123,905 | A * | 9/2000 | Torti et al. | 422/100 |
| 6,136,555 | A * | 10/2000 | Jones | 435/41 |
| 6,146,591 | A | 11/2000 | Miller | 422/65 |
| 6,197,194 | B1 * | 3/2001 | Whitmore | 210/321.8 |
| 6,318,158 | B1 | 11/2001 | Breen et al. | 73/64.56 |
| 6,374,684 | B1 | 4/2002 | Dority | 73/864.81 |
| 6,391,541 | B1 | 5/2002 | Petersen et al. | 435/5 |
| 6,482,362 | B1 * | 11/2002 | Smith | 422/100 |
| 6,565,815 | B1 | 5/2003 | Chang et al. | 422/198 |
| 6,586,253 | B1 * | 7/2003 | Harrison et al. | 435/7.2 |
| 6,692,968 | B2 * | 2/2004 | Burshteyn et al. | 436/63 |
| 6,694,799 | B2 | 2/2004 | Small | |
| 6,702,990 | B1 * | 3/2004 | Camacho et al. | 422/100 |
| 6,741,174 | B2 | 5/2004 | Rhoades et al. | 340/540 |
| 6,770,246 | B1 * | 8/2004 | Husek | 422/101 |
| 6,905,885 | B2 | 6/2005 | Colston et al. | 436/518 |
| 6,951,147 | B2 | 10/2005 | Call et al. | 73/836.22 |
| 6,977,145 | B2 | 12/2005 | Fouillet et al. | 435/6 |
| 6,998,047 | B1 * | 2/2006 | Kopaciewicz et al. | 210/321.75 |
| 7,005,982 | B1 | 2/2006 | Frank | 340/539.26 |
| 7,006,923 | B1 | 2/2006 | Rubin | 702/19 |
| 7,082,369 | B1 | 7/2006 | Rubin et al. | 702/19 |
| 7,106,442 | B2 | 9/2006 | Silcott et al. | 356/338 |
| 7,228,067 | B2 | 6/2007 | Magni et al. | 392/480 |
| 7,318,911 | B2 * | 1/2008 | Smith | 422/100 |
| 7,329,388 | B2 * | 2/2008 | Guzman | 422/82.01 |
| 7,470,546 | B2 * | 12/2008 | Lehmann | 436/180 |
| 7,491,527 | B2 | 2/2009 | Yuan et al. | |
| 7,713,232 | B2 * | 5/2010 | Uber et al. | 604/93.01 |
| 2001/0032666 | A1 | 10/2001 | Jenson et al. | 136/256 |
| 2001/0036630 | A1 | 11/2001 | Ibrahim | 435/6 |
| 2002/0022261 | A1 | 2/2002 | Anderson et al. | 435/287.2 |
| 2002/0039783 | A1 | 4/2002 | McMillan et al. | 435/287.2 |
| 2002/0142482 | A1 | 10/2002 | Wu et al. | 436/177 |
| 2002/0151044 | A1 * | 10/2002 | Lemonnier | 435/287.9 |
| 2002/0192114 | A1 * | 12/2002 | Lin et al. | 422/68.1 |
| 2003/0038087 | A1 | 2/2003 | Garvin | 210/767 |
| 2003/0073229 | A1 | 4/2003 | Greenstein et al. | 435/287.2 |
| 2003/0215845 | A1 | 11/2003 | Bille | 435/6 |
| 2004/0142488 | A1 * | 7/2004 | Gierde et al. | 436/178 |
| 2004/0197793 | A1 | 10/2004 | Hassibi et al. | 435/6 |
| 2005/0124073 | A1 * | 6/2005 | Freund | 436/177 |
| 2005/0142565 | A1 | 6/2005 | Samper et al. | 435/6 |
| 2005/0227275 | A1 | 10/2005 | Jung et al. | 435/6 |
| 2005/0266585 | A1 * | 12/2005 | Bargh | 436/177 |
| 2006/0079000 | A1 | 4/2006 | Floriano et al. | 436/164 |
| 2006/0257853 | A1 | 11/2006 | Herman | 435/5 |
| 2007/0116607 | A1 | 5/2007 | Wang et al. | 422/83 |
| 2007/0248958 | A1 | 10/2007 | Jovanovich et al. | |
| 2008/0050803 | A1 | 2/2008 | Northrup et al. | 435/287.2 |
| 2008/0069733 | A1 | 3/2008 | Maltezos et al. | |
| 2008/0125330 | A1 | 5/2008 | Cady et al. | 506/17 |

FOREIGN PATENT DOCUMENTS

| | | |
|---|---|---|
| WO | WO 03/070898 A2 | 8/2003 |

OTHER PUBLICATIONS

Office Action dated May 26, 2009, U.S. Appl. No. 11/509,872, 15 pages.

Office Action mailed on Jul. 30, 2009, U.S. Appl. No. 11/510,073, filed Aug. 24, 2006, Applicant; Allen Northrup, 11 pages.

Office Action mailed on Aug. 6, 2009. U.S. Appl. No. 11/352,108, filed Feb. 9, 2006, Applicant; Phillip I. Belgrader, 8 pages.

International Search Report including the Written Opinion. International Application No. PCT/US2009/62067, International Filing Date Oct. 26, 2009, Date of mailing Dec. 18, 2009, 9 pages.

Office Action mailed Jun. 2, 2010 for U.S. Appl. No. 11/478,807, filed Jun. 29, 2006, 16 pages.

Office Action mailed Oct. 25, 2010 for U.S. Appl. No. 11/478,807, filed Jun. 29, 2006, 17 pages.

* cited by examiner

HANDHELD AND PORTABLE MICROFLUIDIC DEVICE TO AUTOMATICALLY PREPARE NUCLEIC ACIDS FOR ANALYSIS

RELATED APPLICATION

This application claims priority of U.S. Provisional application, Ser. No. 60/608,999, filed Sep. 9, 2004, and entitled "A Microfluidic System Using the Silicon Pillar Chip to Automatically Prepare DNA for Real-Time PCR Analysis", by the same inventors. This application incorporates U.S. provisional application, Ser. No. 60/608,999 in its entirety by reference.

FIELD OF THE INVENTION

The invention relates to a method and apparatus for preparing nucleic acids from a sample. In particular, the invention relates to a handheld and portable microfluidic device to automatically prepare nucleic acids for analysis.

BACKGROUND OF THE INVENTION

Analytes, such as nucleic acids from a target organism, are typically part of a larger sample, with the rest of the material within the sample ranging from trace amounts to very abundant. These materials often interfere with or completely prevent detection of the organism and can make quantitative results impossible. Various extraction protocols and devices have been used to purify the sample, most of which are optimized for certain samples and applications, and usually require bench-top equipment used within a laboratory environment by highly skilled personal. Performing such extraction protocols in the field is difficult and often impossible due to logistical complexities associated with taking laboratory equipment out of the laboratory and into the field. A laboratory environment can also be controlled, whereas such control is limited out in the field.

Biological assays are particularly plagued with the added issue of the analyte's stability, viability, or even mutation, within the sample itself or sample purification methodology. Thus, for biological analysis, the challenges include two equally important and interacting factors: accuracy of the analytical method and efficiency of the sample purification for the analyte in the sample matrix. Since sample matrices are highly variable, a universal preparation protocol remains elusive.

The ability to process large volume liquid samples for PCR (polymerase chain reaction) based testing is ubiquitous to many different sample types. Water testing often demands analyses of sample volumes of tens to hundreds of milliliters to compensate for target dilution, with microbes, along with other particulates, typically concentrated into a smaller volume by a series of filtering and centrifugation steps. For air samples, particulates are captured either directly in collection fluid or on a filter and then eluted into a liquid. Soil samples involve suspending the soil in a liquid to release particulates from the soil colloids. Examples of large volume liquid samples include biological samples, such as blood for screening, or pharmaceutical samples for product validation. Samples are taken to a laboratory environment to perform analysis.

SUMMARY OF THE INVENTION

A handheld and portable extraction device utilizes a microfluidic-based system, used in the field or laboratory, to extract and purify an analyte from a fluid-based sample. The handheld and portable extraction device includes a syringe-like device coupled to a purification chip. The syringe-like device is coupled to the purification block preferably using a combination of check valves, filters, and a tee junction. Such a configuration enables drawing a fluid-based sample into a syringe and then forcing the drawn sample through the purification chip at a controlled flow rate. The purification chip is preferably included within a chip block which is removable from the remaining portion of the handheld and portable extraction device. An analyte, such as a nucleic acid, collected within the purification chip can be later removed and analyzed in a variety of ways.

In one embodiment of the present invention a handheld and portable device includes a syringe-like device, a purification chip, a fluidic pathway, and a fluid flow regulator. The syringe-like device draws a fluid-based sample into the handheld and portable device. The purification chip extracts and purifies an analyte from the sample. The fluidic pathway directs the sample from the syringe-like device to the purification chip. The fluid flow regulator regulates a fluid flow of the sample through the purification chip. The syringe-like device also includes a sample collection chamber, a plunger, and a pipette tip. The fluid flow regulator includes a spring coupled to the plunger. The fluid flow regulator also includes one of a group consisting of a pump, a motor, or a $CO_2$ pressure canister. Preferably, the fluid-based sample is a water-based sample. Alternatively, the fluid-based sample is a biological fluid sample or an environmental fluid sample. Preferably, the analyte is a nucleic acid. Alternatively, the analyte is an amino assay.

The handheld and portable device also includes a separator to separate solid debris from the fluid-based sample, wherein the separator is coupled to the syringe-like device and the fluid flow regulator. The separator preferably includes one or more filters. The fluidic pathway preferably includes a check valve and an output connection. The purification chip preferably includes a plurality of pillars, each pillar coated with silicon oxide. A density configuration of the plurality of pillars preferably forms a gradient. The purification chip is preferably included within a chip block, where the chip block also includes microfluidic pathways to and from the purification chip. The chip block is preferably detachable from the handheld and portable device.

In another embodiment of the present invention, a method of preparing a sample in the field includes drawing a fluid-based sample into a handheld and portable device, directing the sample through a fluidic pathway within the device to a purification chip, regulating a fluid flow of the sample through the purification chip, and extracting and purifying an analyte from the sample. The method can also include detaching the purification chip with the nucleic acid from the device. The method can also include separating solid debris from the fluid-based sample prior to extracting and purifying the analyte from the sample.

DETAILED DESCRIPTION OF THE PRESENT INVENTION

Embodiments of a simple, handheld and portable extraction device of the present invention are directed to a microfluidic-based system to be used in the field or laboratory to extract and purify an analyte from a fluid-based sample. As used herein, "fluid" refers to either a gas or a liquid. The fluid-based sample can include a water-based fluid sample, a biological fluid sample, an environmental fluid sample, or any other fluid-based sample in which analytes are to be extracted. An analyte is preferably a nucleic acid. Alternatively, an analyte is an amino assay, including but not limited to proteins, molecules, or whole cells. The handheld and portable extraction device includes a syringe-like device coupled to a purification chip. The purification chip is preferably included within a chip block which is removable from the remaining portion of the handheld and portable extraction device. Analytes, such as nucleic acid, collected within the purification chip can be later removed and analyzed in a variety of ways.

Figure 1:
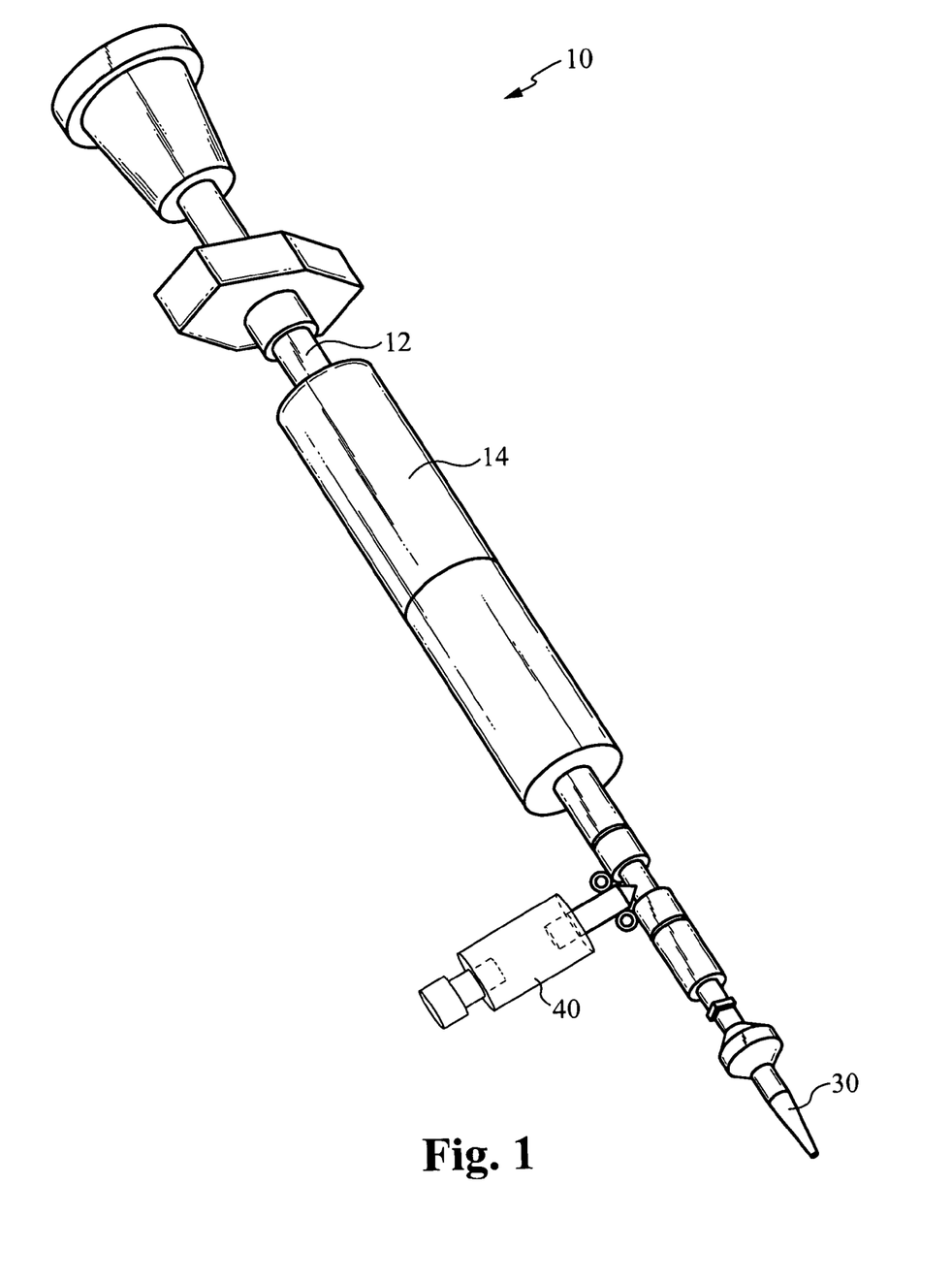
FIG. 1 illustrates a perspective view of a handheld and portable extraction device according to the preferred embodiment of the present invention.

FIG. 1 illustrates a perspective view of a handheld and portable extraction device 10 according to the preferred embodiment of the present invention. The extraction device 10 includes a plunger 12 configured within a syringe barrel 14. The plunger 12 moves in and out of the syringe barrel 14. The syringe barrel 14 is coupled to a pipette tip 30. A chip block 40 is coupled to the syringe barrel 14.

Figure 2:
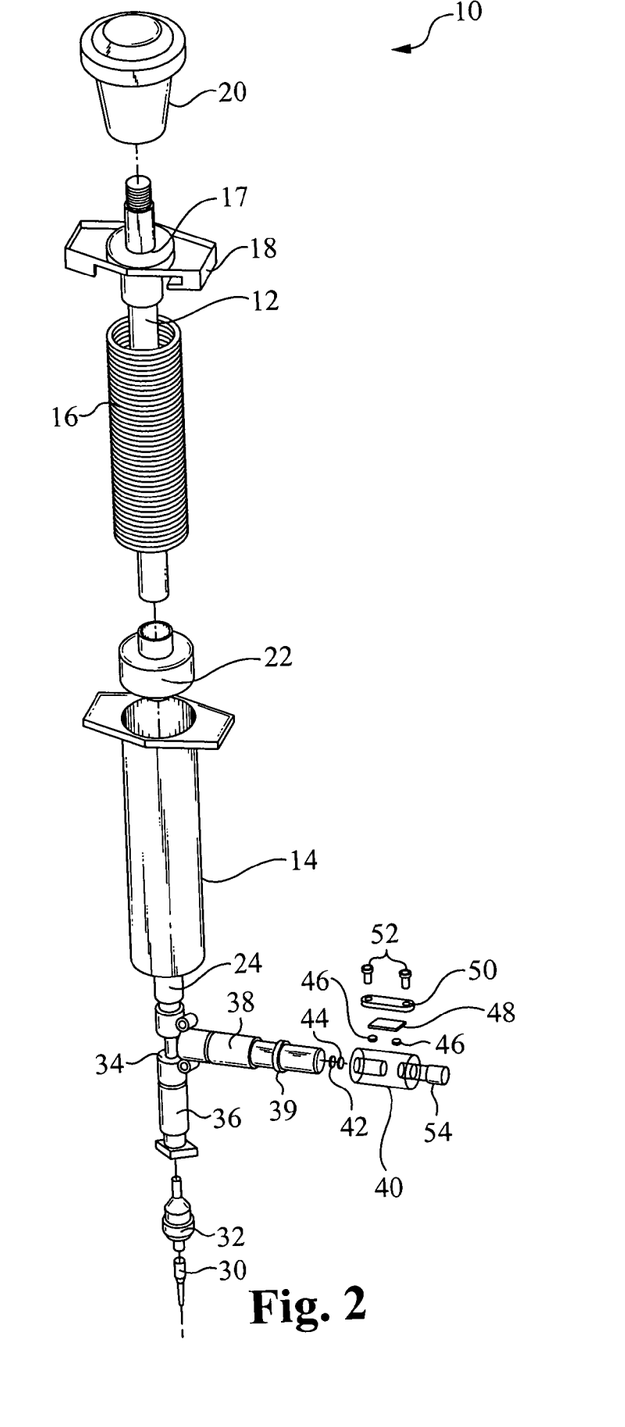
FIG. 2 illustrates an exploded view of the handheld and portable extraction device of FIG. 1.

FIG. 2 illustrates an exploded view of the preferred extraction device 10. The plunger 12 includes a handle 18, a cap 20, and a plunger seal 22. The plunger seal 22 provides a seal between fluid collected in a lower portion of the syringe barrel 14 and an upper portion of the syringe barrel that contains the plunger 12. The handle 18 is secured to the syringe barrel 14. In the preferred embodiment, the handle 18 is secured by a twist lock mechanism as shown. The plunger 12 fits through a central aperture 17 within the handle 18 such that the plunger 12 can move in and out of the syringe barrel 14 while the handle 18 remains secured in place. A spring 16 is coupled to the plunger 12 to bias the plunger 12 inward.

The plunger 12 is preferably moved out of the syringe barrel 14 by manually pulling on the cap 20. Outward movement of the plunger 12 increases a spring compression in the spring 16. Once the cap 20 is released, the spring 16 releases its spring compression thereby forcing the plunger 12 downward through the spring barrel 14.

The syringe barrel 14 also includes a fluid port 24 through which a fluid is aspirated into the syringe barrel 14 upon outward movement of the plunger 12. The fluid port 24 is coupled to a tee junction 34. The tee junction 34 is coupled to an input check valve 36 and an output check valve 38. The input check valve 36 is coupled to a filter holder 32. The filter holder 32 preferably includes a membrane filter (not shown) to separate physical debris from an incoming fluid-based sample. Alternatively, the filter holder 32 includes any type of separating means to separate physical debris from fluid-based sample passing therethrough. The filter holder 32 is coupled to a pipette tip 30.

The output check valve 38 is coupled to the chip block 40 via a threaded nipple 39. The threaded nipple 39 holds an o-ring 42 and a filter 44 against the chip block 40. The filter 44 is preferably a membrane filter similar to the membrane filter included within the filter holder 32. Alternatively, the filter 44 is a frit or any other type of separating means capable of separating physical debris from a fluid-based sample. Although the extraction device 10 is preferably configured to include two filters, a first filter within the filter holder 32 and the second filter 44, it is understood that more, or less, filters can be included within the extraction device 10 to separate physical debris from a fluid-based sample. The chip block 40 is coupled to a waste collector (not shown) via waste connector 54.

Figure 3:
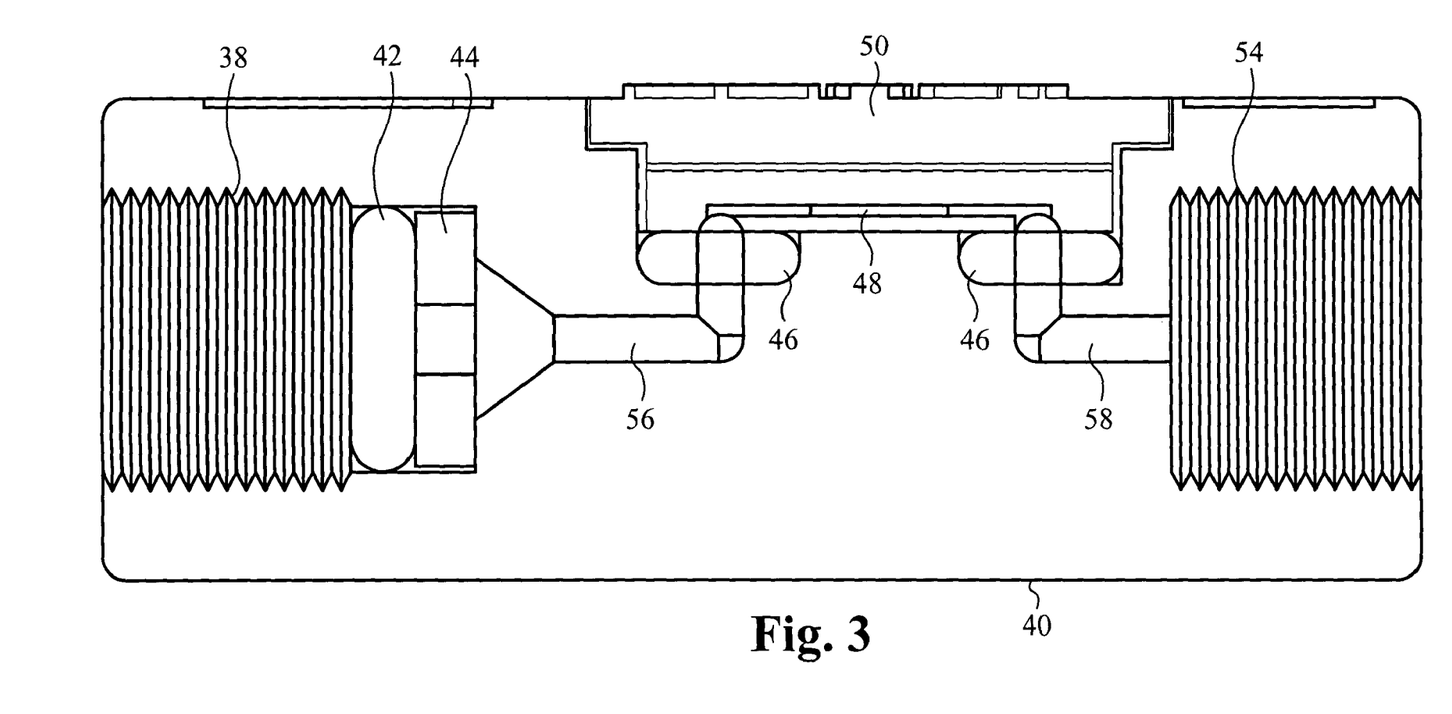
FIG. 3 illustrates a cut-out side view of the chip block in FIG. 1.

The chip block 40 includes a purification chip 48, o-rings 46, a block plate 50, and block plate screws 52, as illustrated in the exploded view in FIG. 2 and also as illustrated in a cut-out side view in FIG. 3. As shown in FIG. 3, the threaded nipple 39 fits within the chip block 40 and against the o-ring 42. The o-ring 42 fits against the filter 44. A microfluidic circuit 56 is coupled to the filter 44 and to an input port of the purification chip 48. A microfluidic circuit 58 is coupled to an output port of the purification chip 48 and the waste connection 54. The waste connection 54 fits within the chip block 40. An o-ring 46 seals the microfluidic circuit 56 to the input port of the purification chip 48, and another o-ring 46 seals the microfluidic circuit 58 to the output port of the purification chip 48.

The purification chip 48 is preferably removable from the chip block 40. The block plate 50 secures the purification chip 48 in position within the chip block 40. The block plate 50 is secured to the chip block 40 using block plate screws 52 (FIG. 2).

Figure 4:
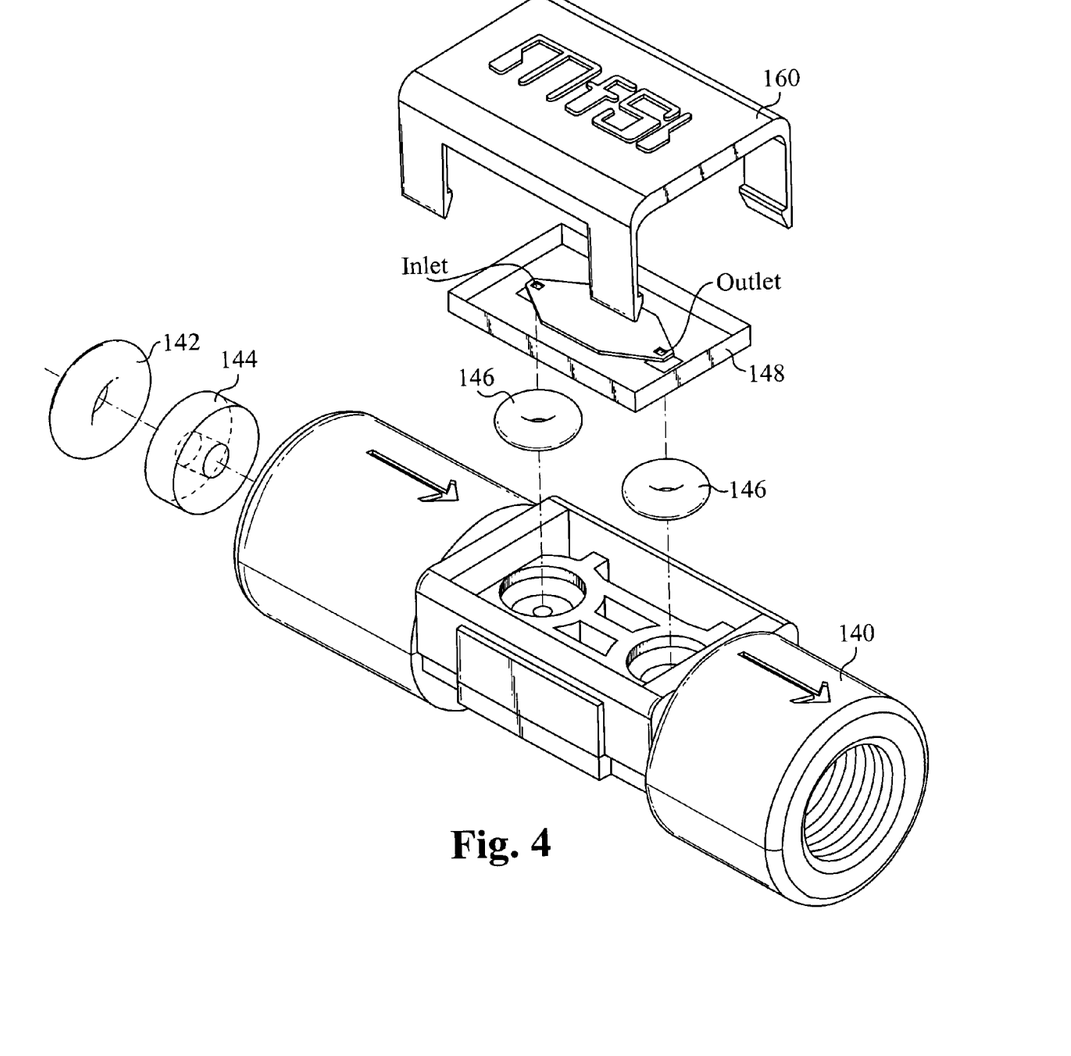
FIG. 4 illustrates an exploded view of an alternative chip block assembly.

FIG. 4 illustrates an alternative embodiment of a chip block 140. The alternative chip block 140 is a molded block configured to receive the output connection threaded nipple 39 (FIG. 2) and the waste connection 54 (FIG. 2). The chip block 140 includes an o-ring 142 and a frit 144 to couple the threaded nipple 39 to the chip block 140. O-rings 146 seal a purification chip 148 to the chip block 140. A cap 160 fits over the purification chip 148 and secures to the body of the chip block 140. The cap 160 and the purification chip 148 are removable. Flow of the fluid-based sample through the chip block 140, including collection of nucleic acid within the purification chip 148, is similar to that described above in relation to the preferred chip block 40 and purification chip 48.

Figure 5:
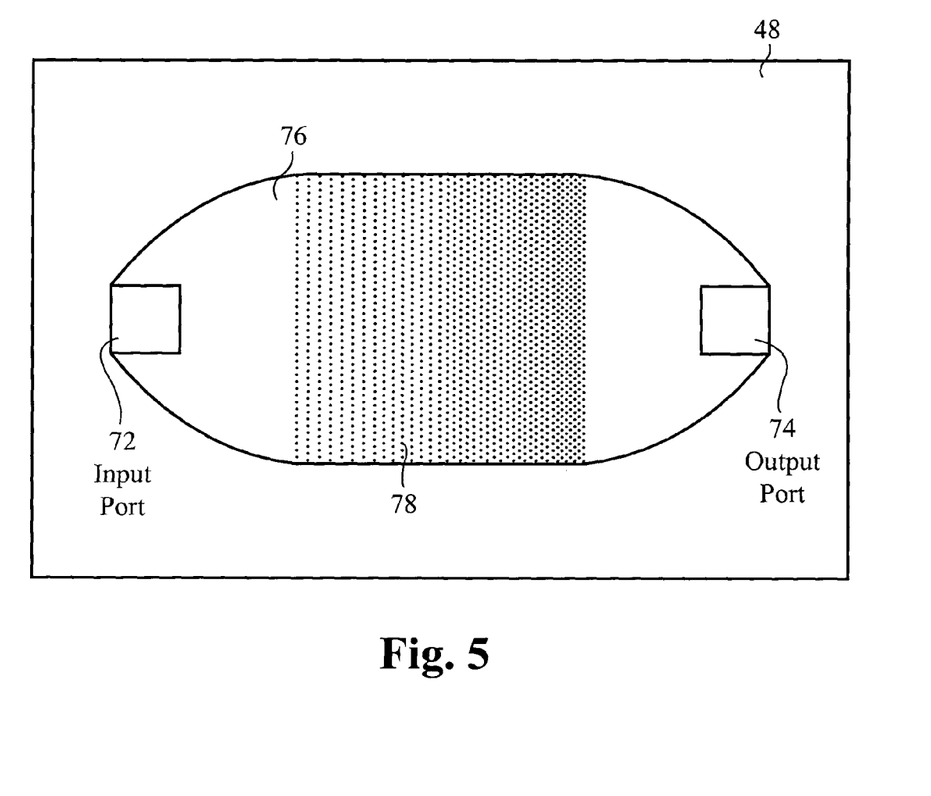
FIG. 5 illustrates a top down view of the purification chip.

FIG. 5 illustrates a top down view of the purification chip 48. The purification chip 48 includes a fluid chamber 76. The fluid chamber 76 includes an input port 72, a plurality of pillars 78, and an output port 74. Fluid-based sample flows from the microfluidic circuit 56 (FIG. 3) into the fluid chamber 76 via the input port 72. The fluid chamber 76 is preferably tear drop shaped such that fluid-based sample entering the fluid chamber 76 disperses outward to interface with the plurality of pillars 78. In the preferred embodiment, the plurality of pillars 78 are configured according to a gradient. That is, a density of the pillars 78 increases from the input port side of the fluid chamber 76 to the output port side. In this manner, there is a higher density of pillars 78 near the output port 74 than there is a density of pillars 78 near the input port 72. The pillars 78 can be arranged in any desired geometrical configuration. Preferably, the pillars 78 are arranged in columns, each column substantially perpendicular to a fluid flow path from the input port 72 to the output port 74. The position of the pillars 78 in each column are preferably staggered between adjacent columns to prevent row alignment of the pillars 78. The gradient can be configured such that the space between adjacent columns progressively narrows from the input port side to the output port side, the number of pillars within each column progressively increases from the input port side to the output port side, or a combination of both configurations. In addition to increasing the extraction efficiency, the gradient acts as a filter to block physical debris present within the fluid-based sample. By positioning the less dense portion of the plurality of pillars 78 near the input port 72, the pillars 78 can more effectively block the debris without becoming clogged. With the debris removed, the fluid-based sample passing the more densely configured pillars 78 is better prepared for nucleic acid extraction and collection.

A surface area of each of the plurality of pillars 78 contacts the fluid-based sample as it flows past. As the fluid-based sample makes contact with the pillar 78, the pillar 78 collects nucleic acid within the fluid-based sample on the surface of the pillar. The plurality of pillars 78 are in general designed to collect an analyte from within a test sample. Exemplary methods of performing such a collection process are described in U.S. Pat. Nos. 5,952,173 and 5,707,799, which are both hereby incorporated by reference. In the preferred embodiment, each pillar 78 is designed to attract nucleic acid to its surface. More preferably, each pillar 78 is designed with a positive charge which acts to attract negatively charged nucleic acid. Each pillar 78 is preferably coated with silicone oxide to provide the positive charge. The fluid flow rate of the fluid-based sample past each of the pillars 78 impacts the effectiveness by which the pillars 78 attract nucleic acid.

The spring 16 is selected such that the spring compression and associated force applied to the fluid-based sample collected within the syringe barrel 14 generates a desired fluid flow rate of the fluid-based sample as it passes the plurality of pillars 78 within the purification chip 48. In an alternative embodiment, the spring 16 is replaced with an alternative means for producing the desired fluid flow rate. For example, air pressure using a $CO_2$ cartridge, a hand pump, or an electrical actuation means such as a motorized screw, is used to apply inward force on the plunger. The potential energy of the applied force is generated either after the fluid-based sample is drawn into the syringe barrel, or generated as the plunger is pulled outward of the syringe barrel to draw in the fluid-based sample. The means for producing the desired fluid flow rate can either be automated or manual. The plurality of pillars 78 collect nucleic acid from the fluid-based sample at peak efficiency based on a select fluid flow rate. Optimum fluid flow rates are determined by experimentation and are dependent on the type of analyte to be collected, the density of the plurality of pillars, the surface composition of the plurality of pillars, the composition of the fluid-based sample, and the like.

Fundamentally, purifying and collecting an analyte from within a sample relies on exploiting differences in physio-chemical properties between the background matrix and the analyte. In the case of nucleic acids, the polymer backbone provides a chain of negative charges at neutral pH. This feature is typically utilized as an adsorption target in most conventional techniques, including the combination of chaotropic agents and random surfaces of glass (packed beds of micro-beads, fibers, particles, etc.) in a plastic device in which the user flows a series of solutions, including the sample. Thus, conventional devices (e.g. Qiagen kits) based on this approach tend to have random surface interactions and flow characteristics.

Single crystal silicon, used routinely in the semiconductor industry, can be formed using the same type of equipment and processes to create micron and sub-micron structures such as found in conventional MEMS (micro-electro-mechanical systems) devices. As applied to the preferred embodiment of the present invention, the surfaces of the pillars 78 are chemically modified to exploit the physio-chemical differences between the analyte (nucleic acid) and the sample matrix (fluid-based sample), and since the structure size and shape can be designed, the microfluidic aspects are also modified and controlled to enhance extraction. The combination of micro-structured surfaces with microfluidic properties that are designed and tested allows for new sample purification devices, such as the handheld and portable extraction device of the present invention and used in a variety of applications, such as extraction and concentration of nucleic acids, amino assays, or other analytes. The glass-surface nature of the oxidized single crystal silicon structures lends itself to the application of the silicon oxide-mediated binding methods to adsorb nucleic acids.

The purification chip used within the extraction device of the present invention is preferably designed to exploit the benefits of silicon structures for nucleic acid extraction, purification and concentration. The properties of the purification chip including flow-through characteristics, high-surface area, and low-fluid volume allow for processing large sample volumes and reducing the extracted nucleic acids into very small volumes, act to yield high concentration effects.

Operation of the extraction device 10 is described in relation to FIGS. 2, 3, and 5. The pipette tip 30 is placed within a fluid-based sample. The plunger 12 preferably starts in a down position where the plunger seal 22 is positioned at the bottom of the syringe barrel 14 against the fluid port 24. To draw the fluid-based sample into the extraction device 10, the plunger 12 is moved outwardly within the syringe barrel 14 by pulling on the cap 20. Outward movement of the plunger 12 aspirates fluid-based sample into the pipette tip 30 through the filter holder 32 to the input check valve 36. As the plunger 12 is pulled outwardly of the syringe barrel 14, the check valve 36 directs the input fluid-based sample from the input check valve 36 to the fluid port 24. The fluid-based sample flows through the fluid port 24 and into the syringe barrel 14. As the plunger 12 is pulled outward, the output connection check valve 38 prevents any backflow of fluid or air through the output path.

As the plunger 12 is pulled outward, spring compression in the spring 16 increases. The plunger 12 is preferably pulled outward until the spring 16 prevents any further outward movement. At this maximum outward position, a maximum spring compression is substantially reached. Alternatively, the plunger 12 is pulled outward to a position that is less than the maximum outward position such that the plunger 12 remains within the syringe barrel 14.

The cap 20 is then released, whereby the spring 16 forces the plunger 12 into the syringe barrel 14. As the plunger 12 moves downward into the syringe barrel 14, the check valve 36 directs the fluid-based sample forced out of the fluid port 24 into the output check valve connection 38 and prevents the sample from flowing back out the inlet path. The fluid-based sample flows through the output check valve connection 38 to the chip block 40.

Within the chip block 40, the fluid-based sample is directed from the output connection 38 through microfluidic circuit 56 and into the fluid chamber 76 of the purification chip 48 via the input port 72. The fluid-based sample flow past the plurality of pillars 78 within the fluid chamber 76 to the output port 74. As the fluid-based sample flows past the plurality of pillars 78, nucleic acid within the fluid-based sample is collected on the surface of the plurality of pillars 78. The fluid-based sample that reaches the output port 74 is directed from the output port 74 to waste connection 54 via microfluidic circuit 58. The waste connection 54 is preferably coupled to a waste collector, where the collected fluid-based sample is treated as waste. Alternatively, fluid-based sample that reaches the waste connection 54 can be collected to be processed again through the extraction device 10.

Figure 6:
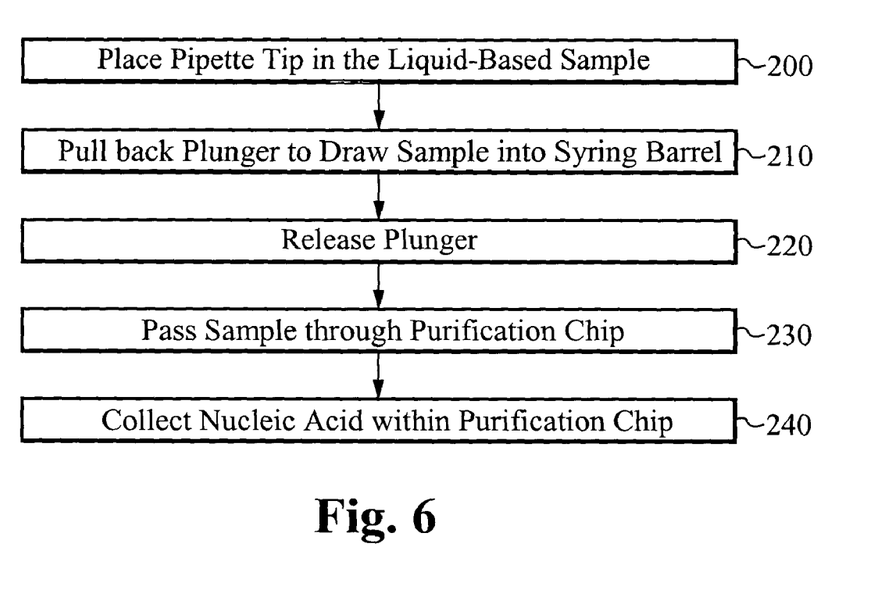
FIG. 6 illustrates a method of operating the handheld and portable extraction device of the present invention.

Operation of the extraction device 10 is generalized in the method illustrated in FIG. 6. In the step 200, the pipette tip 30 is placed in the fluid-based sample. In the step 210, the plunger 12 is pulled back to draw the fluid-based sample into the syringe barrel 14. In the step 220, the plunger 12 is released. Upon release of the plunger 12, the spring 16 coupled to the plunger 12 exerts a pressure on the fluid-based sample drawn into the syringe barrel 14. In response to the induced pressure, the fluid-based sample is forced out of the syringe barrel 14 and into the purification chip 48. At the step 230, the fluid-based sample passes through the purification chip 48. At the step 240, an analyte, such as nucleic acid, is collected within the purification chip 48 and the remaining fluid-based sample passes through as waste. Steps 200-240 can be repeated multiple times to process larger volumes of fluid.

The extraction device 10 is designed such that the chip block 40 is removable. In the preferred embodiment, the threaded nipple 39 screws into the chip block 40, and the chip block 40 is removable by unscrewing the chip block 40 from the threaded nipple 39. Alternatively, the threaded nipple 39 snaps into the chip block 40, and the chip block 40 is removable by pulling the chip block off of the threaded nipple 39. Still alternatively, the threaded nipple 39 is made of a breakable material such that the chip block 40 is removed by breaking in two the threaded nipple 39. Alternatively, any method of removably coupling the chip block 40 to the threaded nipple 39 can be used.

Once the fluid-based sample passes through the purification chip 48, the purification chip 48 is preferably disconnected from the extraction device 10 to remove any collected nucleic acid from within the purification chip 48.

Figure 7:
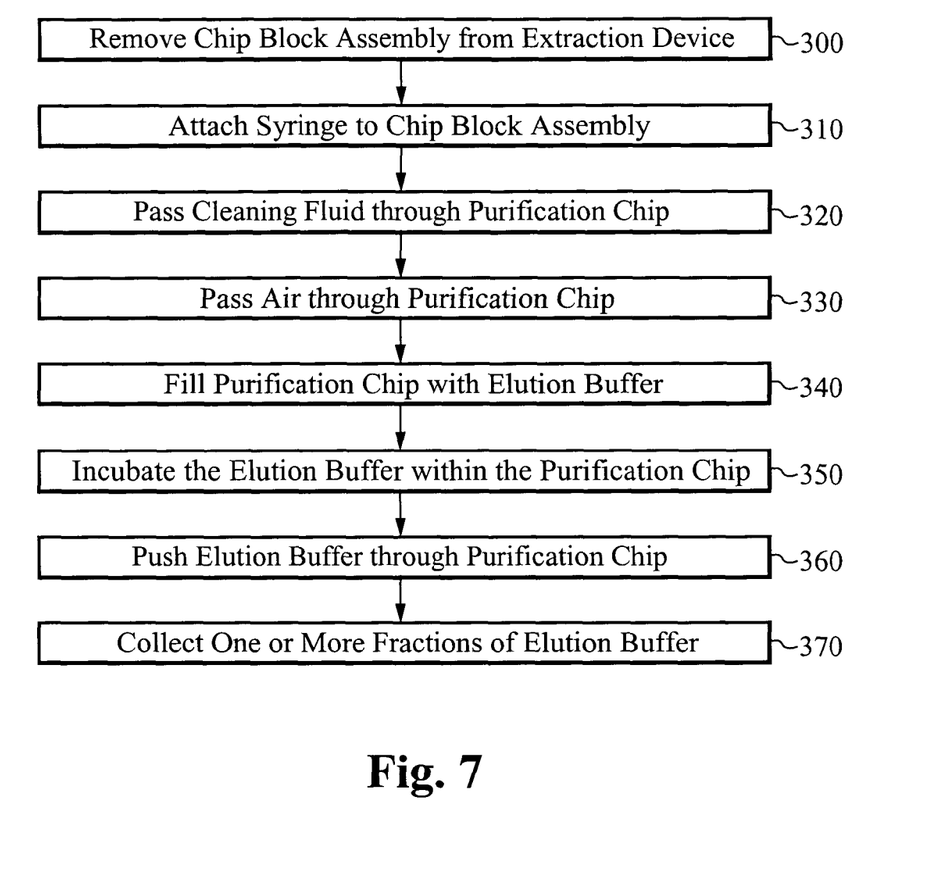
FIG. 7 illustrates a method of removing nucleic acid collected from within the purification chip.

FIG. 7 illustrates a method of removing nucleic acid from within the purification chip 48. At the step 300, the chip block 40 is removed from the extraction device 10. At the step 310, a syringe is attached to the chip block 40. In the preferred embodiment, the syringe is fitted to the chip block 40 at the same opening as the output connection 38 of the extraction device 10. In such a configuration, the syringe is able to deliver a liquid to the purification chip 48 through the input port 72. At the step 320, a cleaning fluid is delivered from the syringe to and through the purification chip 48. Passing the cleaning fluid through the purification chip 48 substantially removes any collected debris and residual fluid-based sample. The cleaning fluid is preferably water. Alternatively, the cleaning fluid is any liquid sufficient to substantially remove any collected debris and residual fluid-based sample.

At the step 330, the purification chip 48 is substantially cleared of any residual liquid by pushing air through the purification chip 48 using an empty syringe. Multiple iterations can be performed to remove as much liquid as possible. Alternatively, any conventional method can be used to dry the purification chip 48, such as using heat or compressed air. At the step 340, a syringe having an elution buffer is attached to the chip block 40. In the preferred embodiment, the syringe is again fitted to the chip block 40 at the same opening as the output connection 38. The elution buffer is then delivered into the purification chip 48. At the step 350, the elution buffer within the purification chip 48 is incubated for a select time period to elute nucleic acid from the purification chip 48. Preferably, the elution buffer is a sodium hydroxide solution. After the select time period is expired, at the step 360 the elution buffer is pushed through the purification chip 48. At the step 370, one or more fractions of the elution buffer are collected.

Although the handheld and portable extraction device of the present invention has been described in terms of a single iteration of sample extraction while on-site, multiple iterations can be performed. In this case, the fluid-based sample that passes through the purification chip is collected and then drawn back into the extraction device as described above in relation to the first iteration. Any fluid-based sample that passes through the purification chip can be collected and re-drawn into the extraction device any number of iterations. Or, where the fluid-based sample is originally drawn from a sufficiently large source, once the first fluid-based sample passes through the extraction device, another fluid-based sample can be drawn from the source using the same extraction device. Any number of fluid-based samples can be drawn from the original source in this manner. Such a method is useful in the case where a large sample source exists which may include a diluted nucleic acid.

The handheld and portable extraction device has been described above as comprising separate elements fitted together, such as the pipette tip 30, the filter holder 32, the input connection 36, the check valve 34, the output connection 36, and the syringe barrel 14. The present invention also considers that some or all of the elements comprising the extraction device 10 can be integrated together, such as being form molded.

It is understood that the size of the syringe barrel can be larger or smaller depending on the application. As the size of the syringe barrel changes, so too does the force required to achieve the desired fluid flow rate of the fluid-based sample through the purification chip.

In one embodiment, either the block plate 50 (FIG. 4) or the cap 160 (FIG. 5) are optically transparent such that an optical detector (not shown) can be coupled to the block plate 50 or the cap 160 to perform optical analysis on collected analytes within the purification chip 48 or the purification chip 148. In another embodiment, the block plate 50 or the cap 160 can be removed, and the optical detector can be coupled to the purification chip 48 or the purification chip 148 to perform optical analysis.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A handheld and portable device comprising:
   a. a device input opening to the handheld and portable device, the device input opening is configured to provide external access and to input an external fluid-based sample into the handheld and portable device;
   b. a single syringe-like apparatus, wherein the syringe-like apparatus is configured for drawing the fluid-based sample into the device, wherein the syringe-like apparatus includes means for storing the sample input into the device;
   c. first means for directing coupled to the device input opening and to the means for storing, wherein the first means for directing is configured to transport the sample from the device input opening to the means for storing to input the sample into the means for storing;

d. means for extracting and purifying an analyte from the sample, wherein the means for extracting and purifying includes a purification chip having a plurality of pillars, each pillar coated with silicon oxide;

e. second means for directing coupled to the means for storing and to the means for extracting and purifying, wherein the second means for directing is configured to transport the sample from the means for storing into the means for extracting and purifying, further wherein the first means for directing, the means for storing, the second means for directing, and the means for extracting and purifying are configured to transport the sample into the means for storing prior to the sample entering the means for extracting and purifying; and f. means for regulating coupled to the means for storing, wherein the means for regulating is configured to regulate a fluid flow rate of the sample through the means for extracting and purifying.

2. The handheld and portable device of claim 1 wherein the syringe-like apparatus further comprises a plunger coupled to the means for storing, and a pipette tip coupled to the device input opening and to the means for storing, and the means for storing comprises a sample collection chamber.

3. The handheld and portable device of claim 2 wherein the means for regulating includes a spring coupled to the plunger.

4. The handheld and portable device of claim 2 wherein the means for regulating includes one of a group consisting of a pump, a motor, or a $CO_2$ pressure canister.

5. The handheld and portable device of claim 1 further comprising means for separating to separate solid debris from the fluid-based sample, wherein the means for separating is coupled to the means for drawing and the means for directing.

6. The handheld and portable device of claim 5 wherein the means for separating includes one or more filters.

7. The handheld and portable device of claim 1 wherein the first means for directing includes a first check valve and the second means for directing includes a second check valve.

8. The handheld and portable device of claim 1 wherein a density of the plurality of pillars is greater at an output port side of the purification chip than at an input port side of the purification chip.

9. The handheld and portable device of claim 1 wherein the means for extracting and purifying further comprises a chip block including the purification chip and microfluidic pathways coupled to and from the purification chip, wherein the microfluidic pathway coupled to the purification chip is also coupled to the means for directing.

10. The handheld and portable device of claim 9 wherein the chip block is detachable from the handheld and portable device.

11. The handheld and portable device of claim 7 further comprising a tee-junction having a first fluid port, a second fluid port, and a third fluid port, wherein the first fluid port is coupled to the first check valve, the second fluid port is coupled to the means for storing, and the third fluid port is coupled to the second check valve.

12. The handheld and portable device of claim 11 wherein a portion of the tee junction is included in and common to both the first means for directing and the second means for directing.

13. The handheld and portable device of claim 11 wherein the second means for directing includes a connector having a fluid conduit extending through the connector from a first end to a second end, wherein the first end is coupled to the second check valve and the second end is coupled to the means for extracting and purifying.

14. The handheld and portable device of claim 13 further comprising a pipette tip coupled to the first check valve, wherein the pipette tip includes the device input opening.

15. A handheld and portable device comprising:

a. a device input opening to the handheld and portable device, the device input opening is configured to provide external access and to input an external fluid-based sample into the handheld and portable device;

b. a syringe-like device to draw the fluid-based sample into the device, wherein the syringe-like device includes a sample collection chamber to store the sample;

c. a first fluidic pathway coupled to the device input opening and to the sample collection chamber to transport the sample from the device input opening into the sample collection chamber, wherein the first fluidic pathway includes a first check valve;

d. a purification chip to extract and purify an analyte from the sample;

e. a second fluidic pathway coupled to the sample collection chamber and to the purification chip to transport the sample from the sample collection chamber into the purification chip, wherein the first fluidic pathway, the sample collection chamber, the second fluidic pathway, and the purification chip are configured to transport the sample into the sample collection chamber prior to the sample entering the purification chip, wherein the second fluidic pathway includes a second check valve; and f. a fluid flow regulator coupled to the syringe-like device to regulate a fluid flow rate of the sample through the purification chip.

16. The handheld and portable device of claim 15 wherein the syringe-like device further includes a plunger coupled to the sample collection chamber and a pipette tip coupled to the device input opening and the sample collection chamber.

17. The handheld and portable device of claim 16 wherein the fluid flow regulator includes a spring coupled to the plunger.

18. The handheld and portable device of claim 16 wherein the fluid flow regulator includes one of a group consisting of a pump, a motor, or a $CO_2$ pressure canister.

19. The handheld and portable device of claim 15 further comprising a separator to separate solid debris from the fluid-based sample, wherein the separator is coupled to the syringe-like device and the fluid flow regulator.

20. The handheld and portable device of claim 19 wherein the separator includes one or more filters.

21. The handheld and portable device of claim 15 wherein the purification chip includes a plurality of pillars, each pillar coated with silicon oxide.

22. The handheld and portable device of claim 21 wherein a density of the plurality of pillars is greater at an output port side of the purification chip than at an input port side of the purification chip.

23. The handheld and portable device of claim 15 further comprises a chip block including the purification chip and microfluidic pathways coupled to and from the purification chip, wherein the microfluidic pathway coupled to the purification chip is also coupled to the second fluidic pathway.

24. The handheld and portable device of claim 23 wherein the chip block is detachable from the handheld and portable device.

25. The handheld and portable device of claim 15 further comprising a tee-junction having a first fluid port, a second fluid port, and a third fluid port, wherein the first fluid port is coupled to the first check valve, the second fluid port is coupled to the sample collection chamber, and the third fluid port is coupled to the second check valve.

26. The handheld and portable device of claim 25 wherein a portion of the tee junction is included in and common to both the first fluidic pathway and the second fluidic pathway.

27. The handheld and portable device of claim 25 wherein the second fluidic pathway includes a connector having a fluid conduit extending through the connector from a first end to a second end, wherein the first end is coupled to the second check valve and the second end is coupled to the purification chip.

28. The handheld and portable device of claim 27 further comprising a pipette tip coupled to the first check valve, wherein the pipette tip includes the device input opening.

* * * * *